United States Patent
Hofmann (10) Patent No.: US 10,660,783 B2
(45) Date of Patent: May 26, 2020

(54) OCCLUSAL SPLINT ARRANGEMENT

(71) Applicant: Konrad Hofmann, Thüngersheim (DE)

(72) Inventor: Konrad Hofmann, Thüngersheim (DE)

( * ) Notice: Subject to any disclaimer, the term of this patent is extended or adjusted under 35 U.S.C. 154(b) by 474 days.

(21) Appl. No.: 15/129,134

(22) PCT Filed: Feb. 24, 2015

(86) PCT No.: PCT/EP2015/053792
§ 371 (c)(1),
(2) Date: Sep. 26, 2016

(87) PCT Pub. No.: WO2015/144374
PCT Pub. Date: Oct. 1, 2015

(65) Prior Publication Data
US 2018/0168845 A1    Jun. 21, 2018

(30) Foreign Application Priority Data
Mar. 28, 2014    (DE) .................. 10 2014 104 408

(51) Int. Cl.
*A61F 5/058* (2006.01)
*A61F 5/56* (2006.01)
*A61C 7/36* (2006.01)

(52) U.S. Cl.
CPC .......... *A61F 5/05891* (2013.01); *A61F 5/566* (2013.01); *A61C 7/36* (2013.01)

(58) Field of Classification Search
CPC ........ A61F 5/05891; A61F 5/56; A61F 5/566; A61F 2005/563; A61F 5/58;
(Continued)

(56) References Cited

U.S. PATENT DOCUMENTS 4,130,921 A * 12/1978 Wallshein ................ A61C 7/00
                                                             29/423
4,527,975 A    7/1985 Ghafari et al.
(Continued)

FOREIGN PATENT DOCUMENTS

WO     2013/143511 A1    10/2012
WO     WO-2015143043 A1 *  9/2015 ............. A61F 5/566

OTHER PUBLICATIONS

PCT English Language Translation of the International Preliminary Report on Patentability, PCT/EP2015/053792, dated Oct. 13, 2016, 10 pages.
(Continued)

*Primary Examiner* — Victoria J Hicks
*Assistant Examiner* — Lindsay A Jeffries
(74) *Attorney, Agent, or Firm* — Quarles & Brady LLP (57) ABSTRACT

An occlusal splint arrangement (01) for sleep apnoea therapy includes a maxillary miniplast splint (02) that can be arranged on the maxillary row of teeth and a mandibular miniplast splint (12) that can be arranged on the mandibular row of teeth. The miniplast splints (02, 12) each have positioning device (05, 22) that can define the relative position of the miniplast splints (02, 12) towards each other in the longitudinal direction (X). For simple adjustment of the position, exchangeable positioning devices (22) that are mounted on centring pins (15) are used on one of the two miniplast splints (02, 12). A secure attachment of the respective exchangeable positioning devices (22) on the centring pin (15) is realised by a latching connection.

21 Claims, 8 Drawing Sheets (58) Field of Classification Search
CPC ......... A63B 71/085; A61C 5/007; A61C 7/02; A61C 7/023; A61C 7/026; A61C 7/06; A61C 7/08; A61C 7/10; A61C 7/36; F16B 2/243; F16B 5/0642; Y10T 403/59; Y10T 403/591; Y10T 403/598; Y10T 403/60; Y10T 403/606; Y10T 24/45241; Y10T 24/45257; Y10T 24/45262; Y10T 24/45267
USPC ............. 128/862, 848, 859, 861; 16/6; 24/1, 24/3.11, 3.13, 300, 356, 358–360, 371, 24/380, 705, 460, 462, 573.11, 574.1, 24/578.13, 578.14, 595.11, 708.7, 708.9, 24/709.7, 709.8, 711.1, 711.3; 433/5, 6, 433/7, 8, 19, 24, 140; 403/321, 322.1, 403/324, 326, 329; 602/17
See application file for complete search history.

(56) References Cited

U.S. PATENT DOCUMENTS

| 4,571,187 | A | * | 2/1986 | Weissman | A61C 13/30 433/221 |
|---|---|---|---|---|---|
| 4,654,026 | A | * | 3/1987 | Underwood | A61M 5/1418 128/DIG. 26 |
| 6,174,162 | B1 | * | 1/2001 | Pozzi | A61C 7/02 433/141 |
| 2004/0072117 | A1 | * | 4/2004 | Farzin-Nia | A61C 7/20 433/10 |
| 2005/0028826 | A1 | * | 2/2005 | Palmisano | A61F 5/566 128/848 |
| 2005/0162608 | A1 | * | 7/2005 | Spindelbalker | G02C 1/02 351/41 |
| 2006/0019213 | A1 | | 1/2006 | Graham et al. | |
| 2007/0015105 | A1 | * | 1/2007 | Campanello | A61C 9/002 433/74 |
| 2009/0099664 | A1 | * | 4/2009 | Forrester | A61B 17/562 623/21.18 |
| 2010/0016908 | A1 | * | 1/2010 | Martin | A61M 16/0006 607/3 |
| 2011/0270166 | A1 | * | 11/2011 | Martin | A61J 7/0061 604/79 |
| 2011/0294088 | A1 | * | 12/2011 | Bathen | A61C 7/02 433/3 |
| 2013/0112210 | A1 | * | 5/2013 | Stein | A61F 5/566 128/848 |
| 2013/0298916 | A1 | * | 11/2013 | Alvarez | A61F 5/566 128/861 |

OTHER PUBLICATIONS

International Search Report dated May 20, 2015 for International Application No. PCT/EP2015/053792.

* cited by examiner

OCCLUSAL SPLINT ARRANGEMENT

CROSS-REFERENCE TO RELATED APPLICATIONS

This application represents the national stage entry of PCT International Application No. PCT/EP2015/053792 filed Feb. 24, 2015 and claims priority to German Patent Application No. 10 2014 104 408.8 filed Mar. 28, 2014. The contents of this application are hereby incorporated by reference as if set forth in their entirety herein.

The invention relates to an occlusal splint arrangement, in particular for sleep apnoea therapy, comprising a maxillary and a mandibular miniplast splint according to the preamble of claim 1.

In particular for sleep apnoea therapy, different embodiments of occlusal splint arrangements are known from the state of the art. They generally aim at influencing the position of the upper jaw relative to the lower jaw to the effect that the lower jaw as well as the tongue muscle and the soft palate are prevented to an appropriate degree from dropping backwards during deep sleep so that the airways are kept open.

An embodiment that is particularly advantageous for this task is disclosed in document WO 2013/143511 A1. It comprises a maxillary miniplast splint for arrangement on the maxillary row of teeth and a mandibular miniplast splint for arrangement on the mandibular row of teeth. The two miniplast splints each have positioning means with the aid of which the position of the miniplast splints towards each other can be defined. The two miniplast splints are not fixed to one another; instead, the user can move the lower jaw freely to the largest possible extent while wearing the miniplast splints. When the opposing contact surfaces of the miniplast splints meet, the desired positioning of the mandibular miniplast splint relative to the maxillary miniplast splint takes place with the aid of the respective positioning means.

For this purpose, the maxillary miniplast splint carries the positioning means integrally in the molar area on the left and right side, a guiding surface facing outwards and a contact surface facing forwards being present in each case. By comparison, in the corresponding position, the mandibular miniplast splint has positioning means in the shape of a fin, which is positioned on the contact surface of the mandibular miniplast splint. The special feature of the afore-described embodiment compared to the otherwise common occlusal splint arrangement for sleep apnoea therapy is the exchangeability of the positioning means of the mandibular miniplast splint. In the miniplast splint, a centring pin which protrudes beyond the contact surface is anchored on the left and right side in the molar area. An exchangeable positioning means is attached thereto in an exchangeable manner in each case.

This already advantageous embodiment allows a quick and uncomplicated exchange of the positioning means, thus permitting a change of the position of the mandibular miniplast splint relative to the maxillary miniplast splint in the longitudinal direction (X).

Although the known embodiment already provides a particularly advantageous occlusal splint arrangement, which exhibits comfortable wearing behaviour and is effective in sleep apnoea therapy, its implementation, however, regarding in particular the matching of the centring pin and the complementary centring recess present in the exchangeable positioning means, has proved problematic with regard to the reliability of the secure hold of the assembled exchangeable positioning means. In known embodiments, the problem occasionally occurred that the exchangeable positioning means did not sufficiently adhere to the centring pin of the miniplast splint and dropped off unintentionally during handling. In the opposite case, it was often observed that removal of the exchangeable positioning means was sometimes significantly complicated because the selected friction forces between the centring pin and the centring recess had developed an excess value in an uncontrolled fashion.

Hence, it is the objective of the present invention to provide an improvement over the known embodiment, in particular with regard to the fixation of the positioning means.

The set objective is attained by an embodiment according to the invention pursuant to the teaching of claim 1.

Advantageous embodiments are the subject-matter of the dependent claims.

The occlusal splint arrangement is used in particular for sleep apnoea therapy. Although the present embodiment of an occlusal splint arrangement is thus provided primarily for treating sleep apnoea syndrome, this does not prevent the embodiment according to the invention from also being employed for a differently used occlusal splint arrangement. In this regard, the occlusal splint arrangement can also be provided for treating teeth malpositions or as a bite splint for preventing nightly grinding of the teeth or the like.

The generic occlusal splint arrangement comprises a maxillary miniplast splint that can be arranged on the maxillary row of teeth and a mandibular miniplast splint that can be arranged on the mandibular row of teeth. According to the intended use, the maxillary miniplast splint can be brought to bear against the mandibular miniplast splint. To this end, the miniplast splints have opposing contact surfaces which can be brought to bear against each other substantially within the occlusal plane. In a particularly advantageous manner, the contact surfaces are formed to be even; thus, on the one hand, a small structural height is achieved between the rows of teeth when the mouth is closed and, on the other hand, it is possible to change the position of the miniplast splints towards each other within the plane of the contact surface.

For positioning of the miniplast splints towards each other, the maxillary miniplast splint has at least one maxillary positioning means and the mandibular miniplast splint has at least one mandibular positioning means. The type, design and arrangement of the positioning means on the miniplast splints are initially immaterial. At least, the positioning of the miniplast splints relative to each other requires a form fit between the maxillary and mandibular positioning means, which makes the relative position of the miniplast splints towards each other definable in a longitudinal direction and/or in a transverse direction.

In this regard, it is also initially immaterial whether the form fit is formed outside of the mouth prior to placement on the rows of teeth by joining the miniplast splints, for example, or whether a form fit occurs only if the miniplast splints placed on the rows of teeth are brought in contact with each other by closing the mouth. At least, a corresponding form fit between the positioning means is formed at the latest when the teeth are being closed by the miniplast splints bearing against each other so that the relative position of the miniplast splints towards each other is defined. This relative position can comprise the longitudinal direction, i.e. an extension to the front or to the rear from the patient's perspective, or alternatively or simultaneously a relative positioning in a transverse direction. In this regard, it is further initially immaterial for the embodiment according to the invention whether a slight play is provided.

With respect to the mentioned directions, it is to be explained that, from the patient's perspective, the longitudinal direction extends along a line from the rear to the front, the vertical direction being approximately perpendicular to the occlusal plane and, further, the transverse direction extending correspondingly perpendicularly to the vertical direction and perpendicularly to the longitudinal direction, i.e. from the left to the right (and vice-versa) from the patient's perspective.

Generically, the positioning means are intended to be arranged on the respective miniplast splints on the left and on the right side in the molar area of the miniplast splint. This means that at least two positioning means must be present per miniplast splint. This is particularly advantageous in that the structural space required for the positioning means or the required space in the corresponding molar area can be taken up without any particular impairment of the wearing patient. In this regard, it is advantageous (but not imperative) if the positioning means are located at the outer side of the row of teeth. This means that the positioning means are located in the area of the cheek between the teeth and the cheek.

The generic embodiment for allowing a change of the position of the miniplast splints in the longitudinal direction carries the substantial feature that the maxillary and/or mandibular miniplast splint comprises at least two centring pins that protrude from the contact surface. Although it is initially immaterial whether the maxillary miniplast splint or the mandibular miniplast splint comprises the centring pins, it is advantageous, however, if the centring pins are arranged on the mandibular miniplast splint. The centring pins are to be anchored in the miniplast splint on the left side and on the right side in the molar area. Above the contact surface, the centring pin extends approximately in the vertical direction.

The occlusal splint arrangement further includes exchangeable positioning means which have centring recesses that are complementary to the respective centring pins. Corresponding to the presence of a left centring pin and of a right centring pin, thus, at least one left exchangeable positioning means and one right exchangeable positioning means is required. According to the known embodiment, exchangeable positioning means are designed such that they can be attached to the centring pins that are present on the miniplast splint. In this regard, it is provided that the exchangeable positioning means come to bear against the contact surface of the associated miniplast splint. To allow different relative positions between the mandibular and the maxillary miniplast splint, it is further provided that the positioning means attached to the centring pin can be exchanged for another positioning means which has a different geometry. This means that each positioning means that is intended to be attached to the centring pin can effect an individual relative position of the miniplast splints towards each other.

In a simple and advantageous embodiment, the contact surfaces are designed to be completely even so that the occlusal plane also constitutes the contact surface for the exchangeable positioning means. However, this is not an obligatory embodiment. It is equally possible to slightly tilt the contact surface starting from the even shape in the area of the contact of the exchangeable positioning means so that, in connection with a centring pin that is oriented in an inclined manner towards the vertical axis, for example, the contact surface in the area of the exchangeable positioning means has a local angular deviation with respect to the remaining contact surface. This means that the contact surface in the area of the exchangeable positioning means is designed to be inclined in the direction of the transverse direction in correspondence to the angular deviation of the centring pin with respect to the vertical direction.

In correspondence to the option of exchanging the positioning means that are attached to the centring pin, the only possible result is that only a single positioning means can be present per centring pin, which is exchangeable in principle, but no second different positioning means is available to replace it.

According to the invention, the known embodiment is significantly improved in that the centring pin has a latch lug and the centring recess has a latching depression, the latch lug fixing the exchangeable positioning means to the miniplast splint by latching into the latching depression.

By using a latching connection between the miniplast splint having the centring pin and the positioning means having the centring recess, a secure attachment of the exchangeable positioning means is achieved. Although this makes disassembling the exchangeable positioning means more elaborate than it was known in the previous embodiment, the previous problem of matching between the centring pin and the centring recess is solved to the largest possible extent. Now, through the use of a latching connection, a controlled state is created so that the holding forces of the positioning means on the miniplast splint are substantially determined by the design of the latching connection. The centring pin can be produced in a procedurally reliable manner within tight tolerances. Moreover, it has been found that the centring recess, too, can be produced much more easily within controlled tolerances in the relevant area of the latching recess than was the case in the positioning means with the previous tight tolerancing of the centring recess for ensuring the frictional connection. In this regard, all that is required now is the exact tolerancing of the latching depression in the area of the contact surface of the latch lug.

When realising a centring pin having a latch lug, it is particularly advantageous, in particular for economic reasons, if it is formed as one piece. Moreover, it is advantageous to use a metal sheet for production, which is advantageously processed by laser cutting. Thus, a centring pin of high accuracy can be produced, wherein in particular the small dimensions of the centring pin for use in a miniplast splint are to be considered. Moreover, it is particularly advantageous if the metal sheet is a spring steel so that the latching function is advantageously realised by the centring pin, and therein a long-lasting duration of use without losses in latching force can be guaranteed.

To realise the centring pin and for its attachment to the miniplast splint, it is advantageous according to the known embodiment if it has a base portion which is cast into the miniplast splint and a fastening portion which rigidly protrudes beyond the contact surface. Moreover, it is particularly advantageous for realising the latching function if an elastically deformable connecting portion is moulded to the fastening portion, the latch lug being located at the free end of said connecting portion. Thus, the latching function is realised in that an elastic deformation of the connecting portion takes place when joining the positioning means and the miniplast splint, the latch lug subsequently being able to engage into the latching depression while the deformation of the connecting portion is partially or extensively restored.

In particular in connection with the use of a metal sheet, especially made of spring steel, a particularly reliable latching function is made possible by realising an elastic connecting portion.

In contrast, in an advantageous manner, no elastically deformable portion is necessary in the exchangeable positioning means; instead, a substantially non-deforming design of the centring recess including a latching depression can be selected.

However, it would also be conceivable to design the centring pin to be rigid and non-deformable at large so that the latch lug is not deformed and does not give way when the exchangeable positioning means is joined to the miniplast splint by pushing the centring recess onto the centring pin. To realise a latching function, however, a deformability of the exchangeable positioning means is required so that the latch lug can engage into the latching depression following an interim deformation of the exchangeable positioning means in the area of the centring recess. This embodiment, however, is only of special interest in cases where the exchangeable positioning means has to be disassembled only very rarely or only once or is designed as a disposable component and is often replaced by an identical positioning means.

Moreover, alternatively to the embodiment according to the invention, an attachment of the exchangeable positioning means to the centring pin can be realised by a latching function in which the centring pin has a latching depression and the exchangeable positioning means has a latch lug. In particular in a centring pin formed from a metal sheet, a latching depression can be easily produced by a lateral or central recess. On the other hand, the exchangeable positioning means requires a latch lug in the area of the centring recess which protrudes into the centring recess. Said latch lug can also be easily realised in an exchangeable positioning means that is produced as a plastic injection-moulded part, for example, with the aid of a scraper in the tool. In this regard, it must be considered—as in the previous embodiment—that, when joining the exchangeable positioning means to the miniplast splint, an elastic deformation of the exchangeable positioning means takes place as a whole through the latch lug protruding into the centring recess.

To realise an elastically deformable connecting portion, it is possible in a first variation to provide the connection to the rigid fastening portion directly above the contact surface. Correspondingly, the latch lug is located at the end of the centring pin that is remote from the contact surface. However, when joining the exchangeable positioning means, this variation requires the latch lug to be inserted deeply into the centring recess while the connecting portion deforms and thus complicates the assembling process.

In contrast, it is particularly advantageous if the elastically deformable connecting portion is connected to the end of the rigid fastening portion that is remote from the contact surface. Thus, the elastically deformable connecting portion basically begins at the free end of the centring pin. Thereafter, the elastically deformable connecting portion extends along the fastening portion in the direction towards the contact surface. This advantageous embodiment facilitates the assembly of the exchangeable positioning means because in this case the latch lug is located closely to the contact surface and thus, when joining the centring recess and the centring pin, the latch lug has to pass only a short portion with a deformation of the elastic connecting portion before the latch lug can be inserted into the associated latching depression.

To improve the elastic deformation of the connecting portion with a sufficiently large overlapping of the latch lug when being inserted into the centring recess and simultaneously with minimal deformation forces, it is advantageous if the connecting portion is designed to be as long as possible. Thus, it is further particularly advantageous if the elastic connecting portion is adjacent to the rigid fastening portion in such a manner that it first extends around a free eye in a semi-circle by $170°+/-10°$. A shaping in which the connecting portion is first guided around a free eye at an angle of $175°+/-5°$ and then extends approximately parallel to the fastening portion is particularly advantageous. Thus, the length of the elastically deformable connecting portion can be effectively enlarged without requiring an appreciable enlargement of the length of the centring pin.

Further, it is advantageous if, in the unlatched state, a gap widens between the fastening portion and the connecting portion starting from the end of the fastening portion. In the advantageous embodiment with the connecting portion first being guided in a semi-circle around a free eye, the gap extends starting from the free eye to the end of the connecting portion. The widening of the gap between the connecting portion and the fastening portion ensures the elastic deformability of the connecting portion as it approaches the fastening portion when joining the exchangeable positioning means to the miniplast splint.

The advantageous design of the elastically deformable connecting portion with its extension along the fastening portion while considering its latching function leads to a widening shape of the centring pin starting from the point of connection of the connecting portion to the fastening portion in the unlatched state. This means that, in the advantageous embodiment, the centring pin widens starting from its free end in the direction of the contact surface. In contrast, with the positioning means attached to the miniplast splint, a front surface on the fastening portion and a rear surface on the connecting portion advantageously run substantially parallel to each other, the elastic deforming portion correspondingly being elastically deformed starting from an undeformed state and the latch lug holding in a tensioned manner in the latching depression. Consequently, a centring recess that is complementary thereto is a basically straight pocket starting from the contact surface. Slight angular deviations by 1° to 2°, for example, for the purpose of accounting for a draft angle required due to production to realise the centring recess, are irrelevant in this regard.

A straight design of the centring recess (not considering the latching depression) and of the centring pin in the latched state facilitates in particular a secure fixation of the positioning means on the miniplast splint.

In an alternative embodiment, the elastically deformable connecting portion is not designed with a curve starting from an end of the fastening portion, but extends from the end of the fastening portion directly in the direction towards the contact surface. In this regard, it is particularly advantageous if, in the unlatched state, the connecting portion increasingly rises above the fastening portion starting from its beginning at the end of the fastening portion in the transverse direction. This means that the connecting portion is elastically deflected in the transverse direction, wherein it is initially immaterial to which side the deflection takes place. The stability of the fastening portion and the centring function of the centring pin for the exchangeable positioning means are advantageously ensured if the connecting portion is arranged centrally in the centring pin, i.e. surrounded by the fastening portion on both sides. Thus, the shaping of the fastening portion determines the centring recess required for centring in the exchangeable positioning means irrespective of the shaping and the deformation of the connecting portion.

As a general rule, it is to be assumed that it is impossible in particular for ergonomic reasons, i.e. for ensuring maximum wearing comfort, to design the left and the right exchangeable positioning means as identical parts. Considering the position of the centring pin, however, a solution of this kind can be provided, wherein two different positioning variations are conceivable.

In a first solution, the positioning means that is designed as an identical part is used in identical orientation for both the right and the left side. In this case, it is necessary on the one hand that a centre plane running through the centring recess is designed vertical to the contact surface in the area of the exchangeable positioning means, a corresponding design and positioning of the centring pin and of the contact surface being required in the area of the positioning means, said design being symmetrical with respect to the centre plane of the occlusal device. On the other hand, it is necessary that the two outer surfaces of the exchangeable positioning means, which are viewed in the transverse direction, must be designed symmetrical with respect to the centre plane of the exchangeable positioning means so that the centring function of the miniplast splints towards each other in the transverse direction can be ensured when the positioning means are used on both sides. The resulting possible or required design and positioning of the latch lug and of the latching depression is obvious.

In a second solution, the exchangeable positioning means, which is designed as an identical part, is designed to be rotationally symmetrical about a centre axis. The exchangeable positioning means is used on the left and on the right side in a position turned by 180°. In this case, it is necessary on the one hand that a front positioning surface is designed to be rotationally symmetrical to a rear positioning surface on the exchangeable positioning means to define the position of the miniplast splints in the longitudinal direction. Further, for the placement turned by 180° of the positioning means, it must be observed that the centring pin is oriented in the vertical direction or that, at least in case of a symmetrical deviation with regard to the centre plane of the occlusal device, it is only inclined in the transverse direction and not in the longitudinal direction. This means that the centring pin is oriented either in the vertical direction or deviates from the vertical direction in the transverse direction by the same angle on the right and on the left side. The thus resulting possible or required design and positioning of the latch lug and of the latching depression is equally obvious.

Although it is possible, like in the known embodiment, to remove the exchangeable positioning means from the centring pin by hand, it has proved particularly advantageous if a disassembling tool is provided for this purpose. Said disassembling tool has a disassembly pin that can be inserted into a disassembly recess on the exchangeable positioning means. By inserting the disassembly pin into the disassembly recess on the exchangeable positioning means, the exchangeable positioning means can now be pulled off or pushed off by means of the disassembling tool. Thus, the otherwise common removal of the exchangeable positioning means by gripping it between two fingers, which requires high clamping forces to be exerted by the fingers for removal, becomes unnecessary. For easy handling, it is particularly advantageous if the disassembly recess is formed to be continuous and it is thus possible to insert the disassembly pin into the disassembly recess from both sides on the exchangeable positioning means. However, the substantial advantage of the continuous disassembly recess lies in preventing a deposition of dirt particles that are hard to remove.

When realising a disassembly recess, it is further advantageous if the latter extends transversely to the centring recess substantially in the transverse direction. Arranging the disassembly recess directly on the centring recess further makes it possible that inserting the disassembly pin directly causes an unlatching of the latch lug from the latching depression. Accordingly, inserting the disassembly pin into the disassembly recess leads to a deformation of the elastic connecting portion on the centring pin.

In this regard, it is particularly advantageous if the disassembly recess overlaps with the centring recess in the area of the latching depression. Further, it is particularly advantageous if the latching depression is formed directly by a portion of the disassembly recess. An inserted disassembly pin can be brought to bear directly against the latch lug and can cause the latch lug to unlatch from the latching depression even with little force so that, in consequence, an easy removal of the exchangeable positioning means from the miniplast splint is made possible.

The insertion of the disassembly pin into the disassembly recess for deforming the elastic connecting portion is advantageously facilitated if the disassembly pin has a cross-section that tapers towards the free end so that pushing in the disassembly pin basically along an inclined plane leads to a deformation of the elastic connecting portion.

The disassembly of the exchangeable positioning means by using the disassembling tool is further particularly improved if the disassembling tool can be used in a rotating manner to disassemble the exchangeable positioning means. The disassembling tool is rotated about the centre axis of the inserted disassembly pin, a sliding surface of the disassembling tool coming to bear against the contact surface of the miniplast splint. When the disassembling tool is rotated about the centre axis of the disassembly pin, the sliding surface slides along the contact surface and causes the exchangeable positioning means to be pushed off the centring pin.

Although the previous known embodiment and this embodiment according to the invention allow a quick appropriate positioning of the mandibular miniplast splint relative to the maxillary miniplast splint by using exchangeable positioning means, it is advantageous, however, if another adjustment is possible, in particular in the longitudinal direction. For this purpose, the other miniplast splint (without centring pin) is provided with positioning means that can be adjusted in the longitudinal direction. They are to be correspondingly arranged on the left and right side and, together with the exchangeable positioning means, they effect the positioning of the miniplast splints towards each other in the longitudinal direction. Accordingly, the adjustable positioning means are not formed rigidly by the miniplast splint as in the initial form of the occlusal splint arrangement, but are instead arranged adjustably. The adjustment, in this case, is limited to an adjustment of their position with the associated miniplast splint substantially in the longitudinal direction. For adjustment, an adjusting screw is provided in a particularly advantageous manner between the adjustable positioning means and the associated miniplast splint.

In this regard, it is further particularly advantageous if a potentially present disassembling tool comprises an additional adjusting pin for adjusting the adjusting screw. Thus, the disassembling tool present anyway for removing the exchangeable positioning means can also be used to adjust the adjustable positioning means. Thus, for example, a relative change of the position of the miniplast splints towards each other in the longitudinal direction can be performed in millimetre steps by way of the exchange of the exchangeable positioning means, whereas an adjustment within a millimetre is performed by adjusting the adjustable positioning means.

The use of exchangeable positioning means, both in the known embodiment and in the embodiment according to the invention, leads to the problem of a possible mix-up of the exchangeable positioning means for use on the left side of the miniplast splint and on the right side of the miniplast splint, although the mistake is obvious once they have been plugged onto the centring pin. Hence, it is advantageous if the user is given a hint as to which exchangeable positioning means is to be mounted on which of the two centring pins on the left side and on the right side. In this regard, two different designs for labelling have proved advantageous.

In a first embodiment, the exchangeable positioning means of the left side and of the right side are advantageously provided with two different symbols, being advantageously labelled in an obvious manner with the signs "L" and "R". Thus, the user of the exchangeable positioning means can directly identify the side of the miniplast splint on which the respective positioning means are to be assembled.

To preclude any remaining doubt when the miniplast splint is held in the hand, the centring pins on the left side and on the right side are also advantageously provided with two different symbols, the miniplast splint being translucent at least in the area of the centring pin. In this manner, the symbols are directly visible when they are arranged in the base portion of the centring pin that is cast into the miniplast splint so that an association with the positioning means to be assembled becomes possible. It is obvious that it is advantageous to use the signs "L" and "R" as symbols, the centring pins and the exchangeable positioning means further being advantageously provided with matching symbols.

Placing the corresponding symbols on the adjustable positioning means—if present—has largely the same value, wherein it is to be considered that both miniplast splints have to be held in close spatial proximity in the correct position to each other while assembling the exchangeable positioning means.

It is also possible to place the symbols directly on the miniplast splint below the positioning means to be mounted, for example. However, in these cases, the potential additional expense in tool production and in shaping the miniplast splint is to be taken into account.

The relevant function of the exchangeable positioning means is allowing a change of the position of the mandibular miniplast splint relative to the maxillary miniplast splint in the longitudinal direction. Differently exchangeable positioning means are provided for this purpose, each of which has a different position of the centring pin. To avoid a mix-up of the different exchangeable positioning means, it thus is further advantageous if the exchangeable positioning means are provided with symbols and, if belonging together, the right exchangeable positioning means and the associated left exchangeable positioning means that carry the centring recess in the identical position have identical symbols, whereas different exchangeable positioning means for the left side and, likewise, different positioning means for the right side that have respectively different positions of the centring recess are provided with different symbols. In a simple manner, numbers can be used as symbols. Thus, for example, the number 1 can represent the first possible position of an exchangeable positioning means, the number 2 can represent the next possible position of the available exchangeable positioning means, and so on.

Instead of but also additionally to the use of a symbol, it is advantageous for labelling the association of the exchangeable positioning means if a colour labelling is used. For this purpose, the left exchangeable positioning means and the right exchangeable positioning means, at least in sections, are advantageously designed in different colours.

In the following, it is further advantageous if the adjustable positioning means of the left side and of the right side have, at least in sections, a colour that corresponds to the exchangeable positioning means. Thus, the user of the occlusal splint arrangement, when choosing the exchangeable positioning means to be assembled, can directly identify the side on which the respective positioning means is to be assembled, i.e. the left side or the right side.

In case of a colouring of sections, it is particularly advantageous if the respective outer side on the adjustable positioning means and the respective outer side on the assembled exchangeable positioning means have the same colour so that the colour on the exchangeable positioning means and the colour on the adjustable positioning means, lying side by side, is identical when the positioning means is assembled.

To tell apart exchangeable positioning means for the left side and for the right side that have coinciding positions of the centring pin in contrast to telling apart exchangeable positioning means of the left side that do not belong together and exchangeable positioning means of the right side that do not belong together, it is further advantageous if the positioning means that belong together have, in sections, a corresponding colour, whereas positioning means that do not belong together have different colours. Thus, after assembly of the positioning means, a correct match is recognised if the colours lying advantageously on the inner side of the right exchangeable positioning means and of the left exchangeable positioning means correspond, whereas there must be a mistake if the colours are different.

With respect to other advantageous features of the embodiment according to the invention, reference is explicitly made to document WO 2013/143511 A1 mentioned in the introduction, whose advantageous embodiments apply without limit to the present invention as well.

In the following figures, an exemplary occlusal splint arrangement with a latching function is illustrated.

In the figures.

Figure 1:
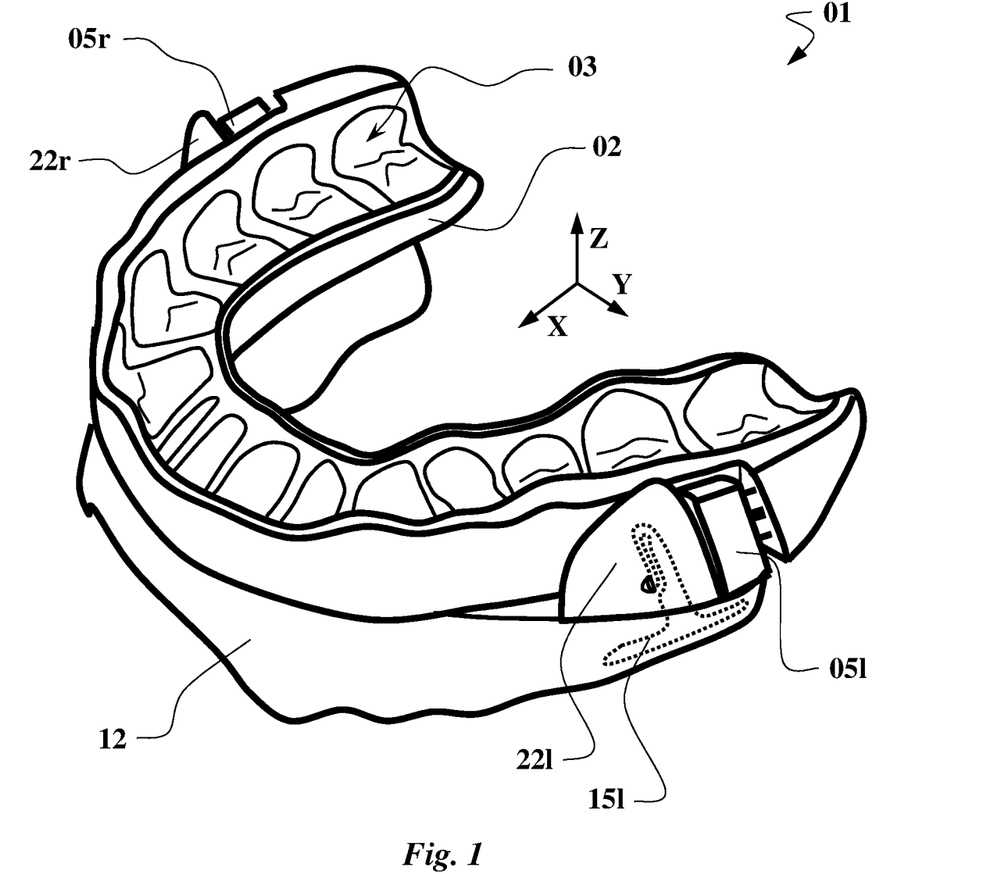
FIG. 1 shows an exemplary embodiment of an occlusal splint arrangement according to the invention in a perspective view.

In FIG. 1, an exemplary occlusal splint arrangement is illustrated. The structure including the maxillary miniplast splint 02 and, on the lower side, including the mandibular miniplast splint 12 is visible. The maxillary miniplast splint 02 has a corresponding teeth receptacle 03 for placement on the maxillary row of teeth. Analogously, the mandibular miniplast splint 12 correspondingly has a teeth receptacle 13 (lying hidden below) for placement of the mandibular miniplast splint 12 on the mandibular row of teeth. Each of these miniplast splints 02, 12 has a positioning means 05 and 22, respectively, on both sides in the molar area. The maxillary positioning means 05r on the right side and 05l on the left side are attached to the maxillary miniplast splint 02 in an adjustable—but not readily exchangeable—manner. In contrast, the mandibular positioning means 22 is embodied as an exchangeable positioning means 22r for the right side and 22l for the left side. Said positioning means 22 are mounted on assembling means in the form of centring pins 15r and 15l, respectively.

The exchangeable positioning means 22 of the mandibular miniplast splint 12 further have guiding surfaces 24 that face inwards, whereas the complementary positioning means of the maxillary miniplast splint 02 are also formed as guiding surfaces 07 by their outer sides. Said guiding surfaces 07, 24 serve to centre and guide the miniplast splints 02, 12 towards each other in the transverse direction (Y). The positioning in the longitudinal direction (X) is realised by means of the positioning surfaces 06 on the adjustable positioning means 05 and on the opposite side interacting with the positioning surfaces 23 at the exchangeable positioning means 22.

The embodiment according to the invention of the centring pin 15 is illustrated, including an elastically deformable connecting portion 18 on whose end the latch lug 19 is located. The latter latches into a latching depression 26, which is in turn formed by the disassembly recess 27, which penetrates the exchangeable positioning means 22 in the transverse direction.

Figure 2:
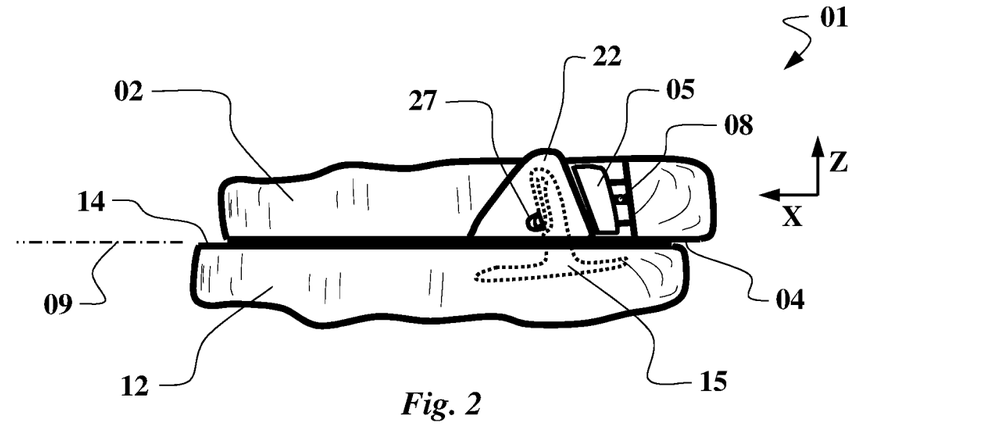
FIG. 2 shows the occlusal splint arrangement in a lateral view.

In FIG. 2, the occlusal splint arrangement 01 of FIG. 1 is illustrated in the lateral view. The arrangement of the contact surfaces 04 of the maxillary miniplast splint 02 on the opposite side of the contact surface 14 of the mandibular miniplast splint 12 is visible, said contact surfaces substantially lying in the occlusal plane 09 when the teeth are closed. Further, it is visible that the maxillary positioning means 05 of the maxillary miniplast splint 02 is located entirely above the contact surface 04, whereas the mandibular positioning means 22 is arranged above the corresponding contact surface 14 on the mandibular miniplast splint 12. Further, the design of the positioning surfaces 06, 23 is visible, which are designed even, first of all, but inclined forwards with respect to the vertical direction (Z). It further (compare FIG. 1) is to be noted that the mandibular exchangeable positioning means 22 is located outside and in front of the maxillary adjustable positioning means 05. Thus, it is ensured that, when the teeth are being closed, the mandibular miniplast splint 12 and thus the lower jaw are pulled forwards for effective sleep apnoea therapy.

The adjustability of the adjustable positioning means 05 is made possible by its displaceable mounting on the maxillary miniplast splint 02, said positioning means being displaceable in the longitudinal direction and an adjusting screw 08 being provided for adjustment.

Figure 3:
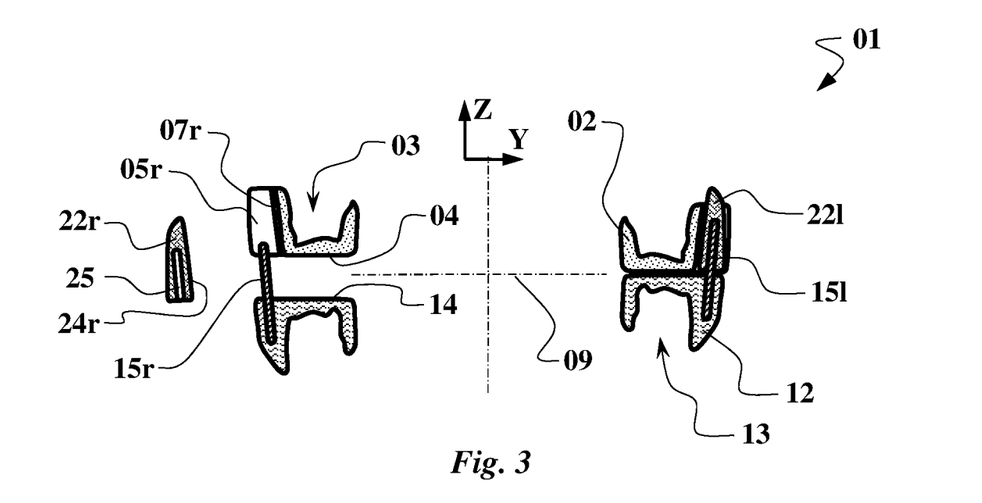
FIG. 3 shows a section through the occlusal splint arrangement.

FIG. 3 additionally illustrates a section through the occlusal splint arrangement 01, the latter being illustrated in an exploded view on the left side and in a stacked arrangement on the right side. Again, the arrangement of the maxillary miniplast splint 02 including the maxillary teeth receptacle 03 and, on the opposite side, of the mandibular miniplast splint 12 including the corresponding teeth receptacle 13 is visible. Said miniplast splints 02, 12 each comprise respective contact surfaces 04, 14 which come into contact in the occlusal plane 09 when the teeth are closed. The relative guiding in the transverse direction (Y) is ensured by means of the guiding surfaces 07, formed by the outer surface of the maxillary miniplast splint 02, in contact with the guiding surfaces 24, formed by the inner side of the exchangeable positioning means 22. Said guiding surfaces 07, 24 are inclined outwards by an angle of inclination 19 with respect to the vertical direction (Z). Thus, it is ensured that the guiding surfaces 07, 24 come together when the teeth are being closed without the mandibular positioning means 22 colliding with the contact surface 04 of the maxillary miniplast splint 02.

Further, the manner of attachment of the exchangeable positioning means 22 to the mandibular miniplast splint 12 by placement of the centring recess 25 on the centring pin 15 is illustrated.

In FIG. 4, again, the maxillary miniplast splint 02 is illustrated in this regard. Once more, the arrangement of the teeth receptacle 03 for placement of the maxillary miniplast splint 02 on the patient's maxillary row of teeth is shown. Further, the positioning means 05r and 05l in the molar area including the positioning surfaces 06 are visible. The positioning means for guiding in the transverse direction are realised by the outer side of the maxillary miniplast splint 02 including the guiding surfaces 07l and 07r. On the lower side (lying hidden), there is the contact surface 04, which here has an even shape and is intended to bear against the respectively other miniplast splint 12.

Figure 4:
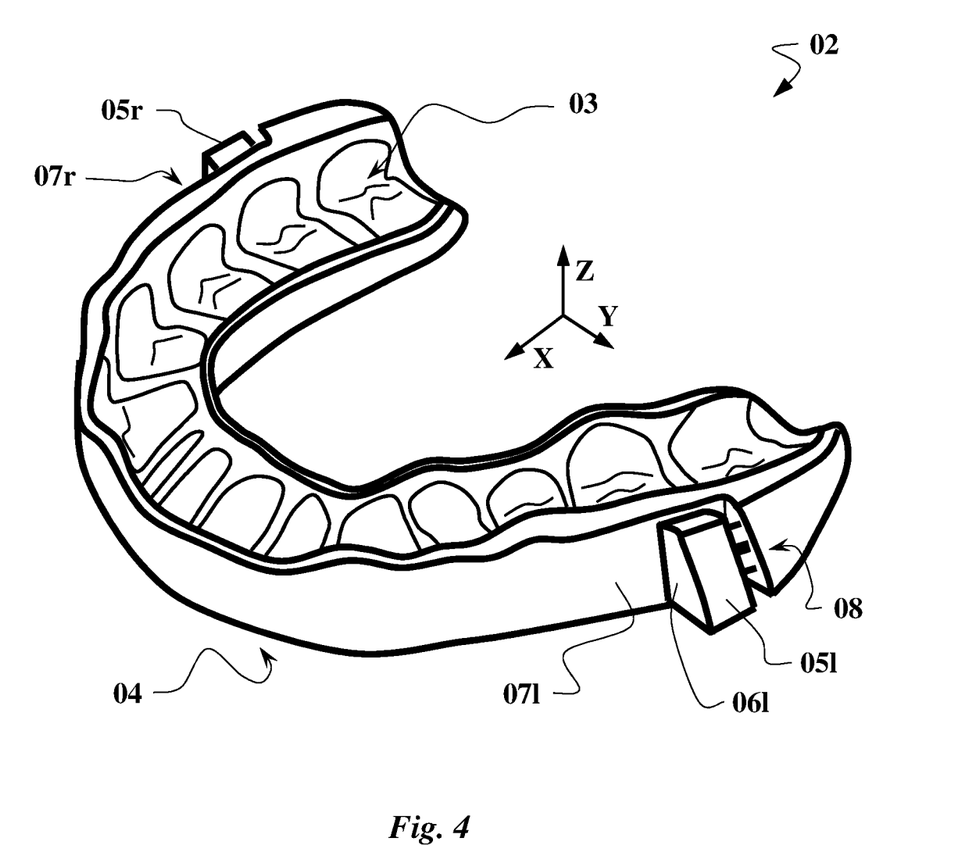
FIG. 4 shows the maxillary miniplast splint for the embodiment of FIG. 1.
Figure 5:
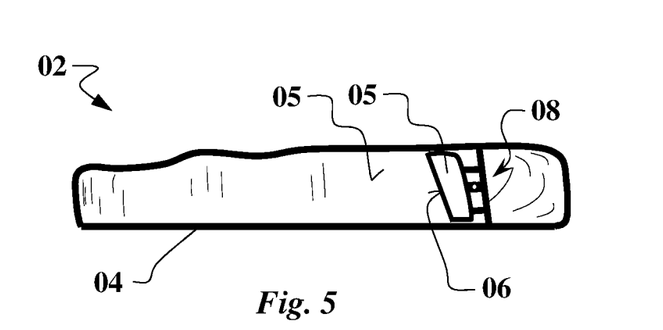
FIG. 5 shows the maxillary miniplast splint in a lateral view.

In FIG. 5, additionally to FIG. 4, the maxillary miniplast splint 02 is illustrated again in the lateral view, including the positioning surface 06 of the maxillary positioning means 05 being oriented in the transverse direction (Y) and in the vertical direction (Z) and the guiding surface 07 being oriented in the longitudinal direction (X) and in the vertical direction (Z).

Figure 6:
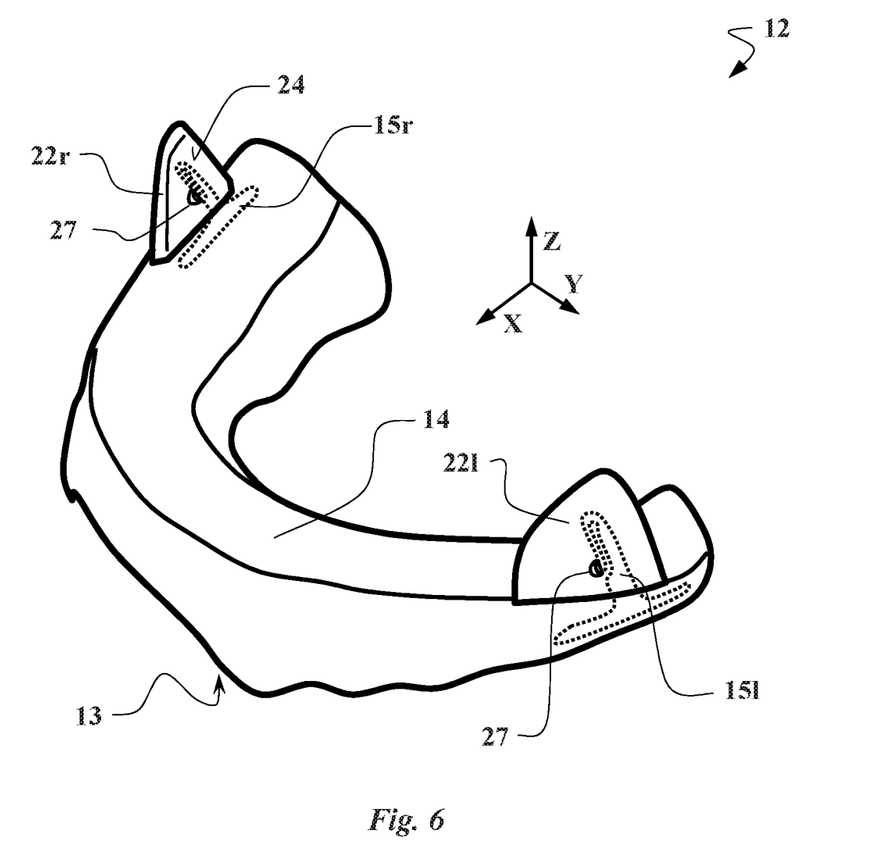
FIG. 6 shows the mandibular miniplast splint for the embodiment of FIG. 1 with exchangeable positioning means.

FIG. 6 illustrates the mandibular miniplast splint 12 from FIG. 1, in which (as in FIG. 1) the teeth receptacle 13 is located at the bottom (hidden). The illustrated top side forms the contact surface 14, which is also formed even and is intended to bear against the maxillary contact surface 04 of the maxillary miniplast splint 02.

The relative position between the miniplast splints 02, 12 is realised here by means of exchangeable positioning means 22r, 22l, which each have a guiding surface 24 that is complementary to the maxillary positioning means 05 and a corresponding complementary positioning surface 23. Further, the illustrated manner of attachment of the positioning means 22 on the mandibular miniplast splint 12 is visible, which takes place by means of centring pins 15l, 15r that are anchored in the base body of the miniplast splint. In this regard, the exchangeable positioning means 22 is present in the manner of a fin, in which the surface facing towards the centre forms the guiding surface 24 and the front edge of the fin lying rearwards forms the positioning surface 23.

Figure 7:
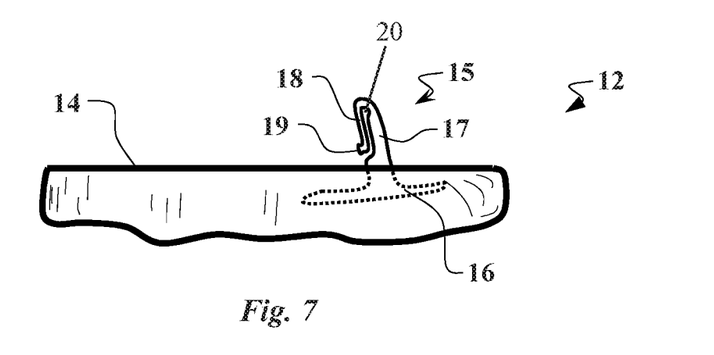
FIG. 7 shows the mandibular miniplast splint in a lateral view.

In addition to FIG. 6, FIG. 7 shows the mandibular miniplast splint 12 in the lateral view, but without its associated positioning means 22. The centring pin 15 is visible, which protrudes beyond the contact surface 14 and whose base portion 16 is anchored in the miniplast splint 12.

In contrast to the known embodiment, this centring pin 15 has a fastening portion 17, which protrudes above the contact surface 14, the connecting portion 18 being adjacent to the free upper end of the centring pin 15. The connecting portion 18 extends in a semi-circle around a free eye 20 and then runs approximately parallel to the fastening portion 17 in the direction towards the contact surface 14. At the free end of the connecting portion 18, there is the projecting latch lug 19.

Figure 8:
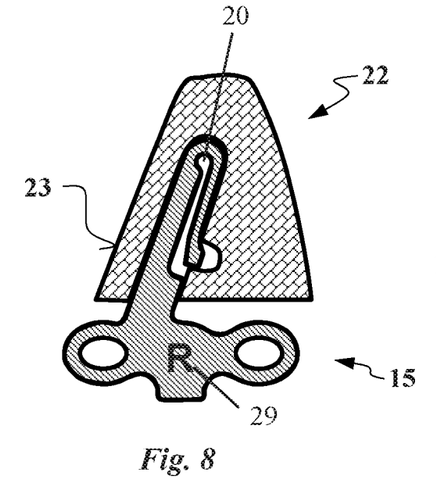
FIG. 8 shows the centring pin of the mandibular miniplast splint with an exchangeable positioning means.

In FIG. 8, the centring pin 15 is illustrated with the assembled exchangeable positioning means 22 in a longitudinal section. For further explanation with regard to the centring pin 15, reference is made to FIG. 9, wherein the exchangeable positioning means 22 is illustrated separately in a section in FIG. 10b.

First of all, the structure of the centring pin 15 including the base portion 16 which is anchored in the miniplast splint 12 is visible. The rigidly arranged fastening portion 17 protrudes from the contact surface 14 and remains substantially undeformed when the exchangeable positioning means 22 is joined. The elastically deformable connecting portion 18 is adjacent to the end of the fastening portion 17 that is remote from the contact surface 14, the connecting portion 18 first extending around a free eye 20 in a semi-circle of about 175°. Then, the elastically deformable connecting portion 18 extends approximately parallel to the fastening portion 17 in the direction towards the contact surface 14. At the free end of the connection portion 18, there is the latch lug 19 which can be inserted into the latching depression 26 of the centring recess 25.

When the positioning means 22 is not assembled, the centring pin 15 slightly widens starting from its free end in the direction towards the contact surface 14, whereas, when the positioning means 22 is assembled, the centring pin 15 is formed with a front edge at the fastening portion 17 substantially parallel to a rear edge at the connecting portion 18. To allow the elastic deformation of the connecting portion 18, a gap starting at the free eye 20 widens towards the end of the connecting portion 18. Thus, the deformability of the connecting portion 18 is ensured when inserting the same into the centring recess 25 to realise the latching function. It can further be taken from the figures that the centring recess 25 extends substantially parallel to a front positioning surface 23 on the exchangeable positioning means 22 and has a substantially constant cross-section. Corresponding to the inclination of the positioning surface 23 on the positioning means 22, the centring recess 25 and thus the centring pin 15 are slightly inclined with respect to the vertical axis (Z).

Figure 10A:
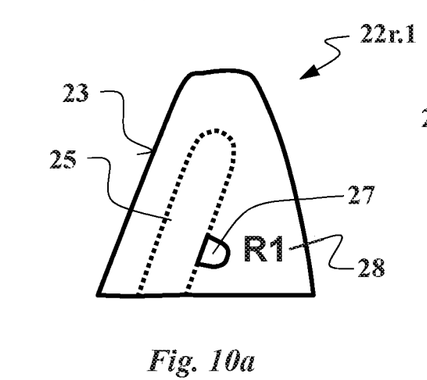
FIG. 10 shows different embodiments of exchangeable positioning means.
Figure 10B:
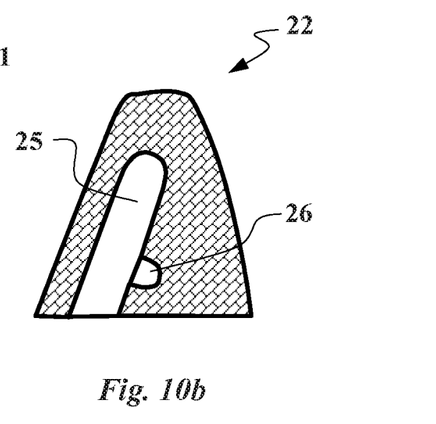

In this advantageous embodiment, the latching depression 26 of the centring recess 25 is formed by a portion of a continuous disassembly recess 27, as can be taken from the combined examination of FIGS. 10a and 10b.

Figure 10C:
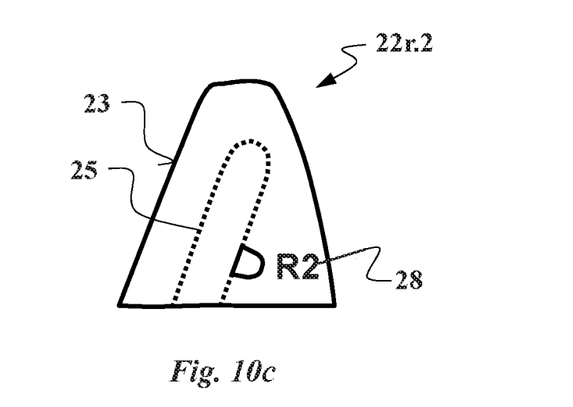

From the comparison of FIGS. 10a and 10c, the different positions of the positioning means 22 on the miniplast splint 12 in the longitudinal direction (X) become apparent. In this regard, the two exemplarily illustrated exchangeable positioning means 22r.1 and 22r.2 show the arrangement of the centring recess 25 in respectively different locations relative to the positioning surface 23.

Figure 9:
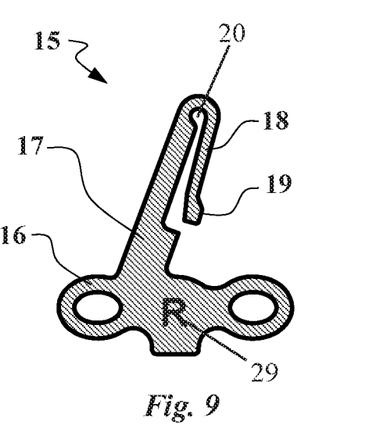
FIG. 9 shows the centring pin of the mandibular miniplast splint.

In FIGS. 8 to 10, the labelling of the centring pin 15 and of the positioning means 22 with the aid of corresponding symbols 29 and 28 is further schematically illustrated, in this case with the symbols 28 and 29 "R" for use on the centring pin 15 for right side of the miniplast splint 12. Further, different symbols 28 are additionally provided in the different embodiments in FIGS. 10a and 10b, the sign "1" being used exemplarily for a first positioning means 22r.1 and the sign "2" for a second positioning means 22r.2 in a series of different positioning means 22.

Figure 11:
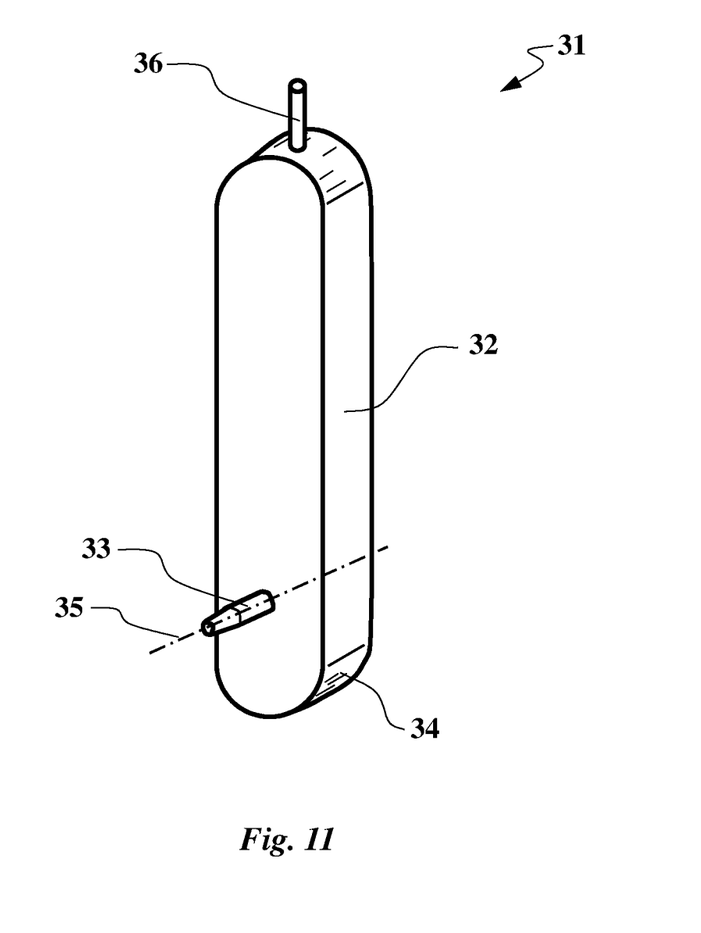
FIG. 11 shows a disassembling tool for disassembling the exchangeable positioning means and for adjusting the adjustable positioning means.

In FIG. 11, an example for a disassembling tool 31 is illustrated, with the aid of which it is possible in a particularly advantageous manner to disassemble the exchangeable positioning means 22 and to advantageously adjust the adjustable positioning means 05. For this purpose, the disassembling tool 31 has a substantially cylindrical disassembly pin 33 on a handle 32, said disassembly pin 33 tapering towards its free end. The disassembly pin 33 forms a centre axis 35 about which the disassembling tool 31 can be rotated at the handle 32 during its use. A pivoting of the handle 32 causes a sliding surface 34 to come into contact with the contact surface 14 at the miniplast splint 12 that is associated with the exchangeable positioning means 22. During rotation of the handle 32 about the centre axis 35, the exchangeable positioning means 22 is pushed off the centring pin 15 of the miniplast splint 12. To this end, it is obviously required that the distance between the sliding surface 34 and the centre axis 35 grow during rotation about the centre axis 35 in contact with the contact surface 14.

In a combined examination of FIG. 8 and FIG. 11, the further advantageous functionality of the disassembling tool 31 becomes apparent. When the disassembly pin 33 is inserted into the disassembly recess 27, the latch lug 19 that is located in the latching depression 26 is displaced by the disassembly pin 33 and is thus caused to unlatch.

In this advantageous embodiment, the disassembling tool 31 further comprises an adjusting pin 36, which can be used to actuate an adjusting screw 08 for adjusting the adjustable positioning means 05.

Figure 12:
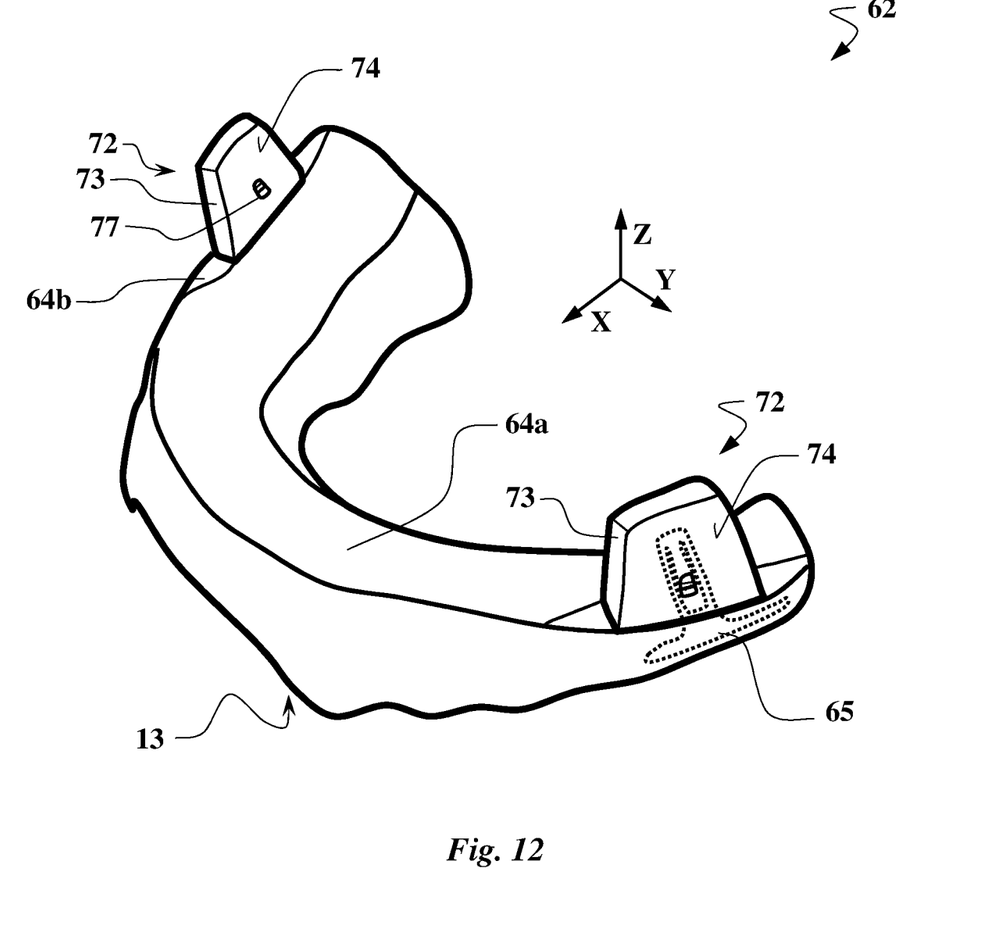
FIG. 12 shows an alternative embodiment of a miniplast splint with exchangeable positioning means.

In FIG. 12, an alternative embodiment for a mandibular miniplast splint 62 is disclosed. Similarly to the previous embodiment, it comprises the exchangeable positioning means 72. In contrast to the previous embodiment, however, the exchangeable positioning means 72 is now designed to be rotationally symmetrical so that it can be utilised both for the left side and for the right side in the identical embodiment. Correspondingly, the exchangeable positioning means has a positioning surface 73 at the front edge as well as a positioning surface 73 at the rear edge. Also, the embodiment example has a guiding surface 74 on the surface facing inwards and on the side facing outwards. To realise a rotationally symmetrical attachment of the exchangeable positioning means to the mandibular miniplast splint 62, the contact surface 64 is slightly inclined as contact surface 64b starting from the largely even contact surface 64a for placement of the maxillary miniplast splint 02 in the area of the exchangeable positioning means 72. The inclination of the inclined contact surface 64b in contrast to the even contact surface 64a corresponds to the angular deviation of the centring pin 65 anchored in the mandibular miniplast splint 62 with respect to the vertical axis (Z). The mandibular miniplast splint exhibits another difference from the previous embodiment example in its changed embodiment of the centring pin 65.

Figure 13:
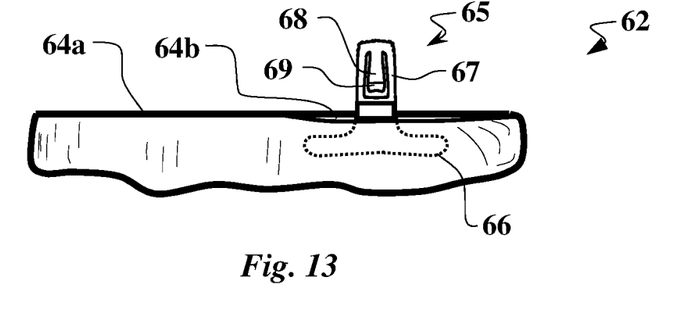
FIG. 13 shows the mandibular miniplast splint in a lateral view.

As can be seen in FIG. 13, the centring pin 65 is also formed by a base portion 66 and a fastening portion 67 adjacent thereto above the contact surface 64. The connecting portion 68 adjacent to the upper end of the fastening portion 67 is also oriented in the direction of the contact surface 64, wherein now, however, the connecting portion 68 is arranged centrally in the centring pin 65 and protrudes from the surface of the fastening portion 67. At the lower end of the connecting portion 68, there again is the latch lug 69 for fixing the exchangeable positioning means 72.

Figure 14:
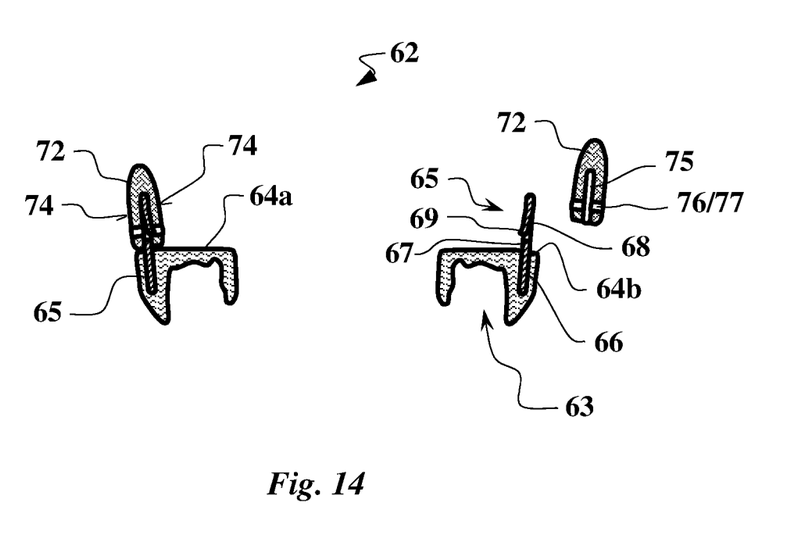
FIG. 14 shows a section through the mandibular miniplast splint with exchangeable positioning means.

In this regard, the subsequent FIG. 14 once more illustrates the mandibular miniplast splint 62 in a cross-section including the exchangeable positioning means 72, wherein it is now visible that the centring pin 65 is slightly inclined with respect to the contact surface 64a, i.e. with respect to the occlusal plane. The contact surface 64b has a corresponding inclination. The inclination of the contact surface 64b merely serves to realise the arbitrary positioning of a rotationally symmetrical exchangeable positioning means 72 so that in both positions its 72 bottom side rests evenly on the contact surface 64b in each case. In this special embodiment example, the exchangeable positioning means 72 is specified to the effect that it 72 can be placed both on the left side and on the right side in whatever orientation, i.e. rotated by 180° in each case, on the centring pin 65. For this purpose, the required latching depressions 76 are arranged on both sides of the central centring recess 75 in the respective exchangeable positioning means 72, said latching depressions 76 being formed analogously to the previous embodiment example by the disassembly recess 77.

LIST OF REFERENCE SIGNS 01 occlusal splint arrangement
02 maxillary miniplast splint
03 teeth receptacle
04 contact surface
05 adjustable positioning means
06 positioning surface
07 guiding surface
08 adjusting screw
09 occlusal plane
12, 62 mandibular miniplast splint
13, 63 tooth receptacle
14 contact surface
64a contact surface for maxillary miniplast splint
64b contact surface for exchangeable positioning means
15, 65 mounting means/centring pin
16, 66 base portion
17, 67 fastening portion
18, 68 connecting portion
19, 69 latch lug
72 rotationally symmetrical exchangeable positioning means
22l right exchangeable positioning means
22r left exchangeable positioning means
23, 73 positioning surface
24, 74 guiding surface
25, 75 centring recess
26, 76 latching depression
27, 77 disassembly recess
31 disassembling tool
32 handle
33 disassembly pin
34 sliding surface
35 centre axis of the disassembly pin
36 adjusting pin
X longitudinal direction
Y transverse direction
Z vertical direction

The invention claimed is:

1. An occlusal splint arrangement for sleep apnea therapy, said arrangement comprising;
a maxillary splint that can be arranged on a maxillary row of teeth, said maxillary splint including a flat first contact surface, the first contact surface configured to extend solely in an occlusal plane;
a mandibular splint that can be arranged on a mandibular row of teeth, said mandibular splint including a flat second contact surface, the second contact surface configured to extend solely in the occlusal plane, wherein the first and second contact surfaces can be brought to bear against each other in the occlusal plane;
a first centering pin which protrudes vertically out of at least one of the first and second contact surfaces in the occlusal plane and is anchored in one of the splints on a left side in a molar area of the one of the splints;
a second centering pin which protrudes vertically out of the at least one of the first and second contact surfaces in the occlusal plane and is anchored in the one of the splints on a right side in the molar area of the one of the splints; and
left and right exchangeable positioners each having a centering recess complementary to the first and second centering pins, respectively, wherein the left and right exchangeable positioners are exchangeably attached to the one of the splints, bearing against the contact surface in the occlusal plane of the one of the splints, a relative position of the splints towards each other being definable in a longitudinal direction (X) and/or in a transverse direction (Y) by way of a form fit between the exchangeable positioners and attached positioners of the other of the splints wherein at least one of the first and second centering pins has a latch lug and the centering recess complementary to the at least one of the first and second centering pins has a latching depression, the latch lug fixing one of the exchangeable positioners on the one of the splints by latching into the latching depression.

2. The occlusal splint arrangement according to claim 1, in which at least one of the centering pins is formed as one piece, and/or the at least one of the centering pins is produced from a metal sheet.

3. The occlusal splint arrangement according to claim 1, in which at least one of the centering pins has a base portion cast into the one of the splints and a fastening portion rigidly protruding beyond the contact surface of the one of the splints, an elastically deformable connecting portion being moulded thereto at whose free end the latch lug is arranged.

4. The occlusal splint arrangement according to claim 3, in which starting from an end of the fastening portion that is distant from the contact surface of the one of the splints, the elastically deformable connecting portion extends along the fastening portion in a direction towards the contact surface of the one of the splints.

5. The occlusal splint arrangement according to claim 4, in which the elastically deformable connecting portion is adjacent to the rigid fastening portion and, beginning from the rigid fastening portion, the connecting portion extends in a bent shape around a free eye by 170°±10°.

6. The occlusal splint arrangement according to claim 5, in which in an unlatched state, a gap widens between the fastening portion and the connecting portion starting from the end of the fastening portion.

7. The occlusal splint arrangement according to claim 4, in which in a latched state, a front surface on the fastening portion and a rear surface on the connecting portion run substantially parallel to each other.

8. The occlusal splint arrangement according to claim 4, in which in an unlatched state, the connecting portion increasingly rises with respect to the fastening portion in the transverse direction (Y) starting from the end of the fastening portion.

9. The occlusal splint arrangement according to claim 1, in which at least one of the exchangeable positioners has at least one continuous disassembly recess into which a disassembly pin of a disassembling tool can be inserted to remove the at least one of the exchangeable positioners from the one of the splints.

10. The occlusal splint arrangement according to claim 9, in which a central axis of the disassembly recess is oriented perpendicularly to a central axis of the centering recess, an inserted disassembly pin configured to cause the latch lug to latch out of the latching depression.

11. The occlusal splint arrangement according to claim 9, in which the disassembly recess intersects the centering recess in an area of the latching depression, wherein the latching depression is formed by a portion of the disassembly recess, an inserted disassembly pin configured to bear against the latch lug thereby causing the latch lug to latch out of the latching depression.

12. The occlusal splint arrangement according to claim 9, in which a free end of the disassembly pin has a tapering cross-section.

13. The occlusal splint arrangement according to claim 9, in which after the disassembly pin has been inserted into the disassembly recess, a sliding surface of the disassembling tool can come to bear against the contact surface of one of the splints, the at least one of the exchangeable positioners configured to be pushed off the at least one of the first and second centering pins by a rotation of the disassembling tool about a center axis of the inserted disassembly pin.

14. The occlusal splint arrangement according to claim 1, in which on the left side and on the right side, each attached positioner of the other of the splints is substantially adjustable in the longitudinal direction (X).

15. The occlusal splint arrangement according to claim 1, in which each attached positioner is adjustable by adjusting an adjusting screw, an adjusting pin for adjusting the adjusting screw being arranged on a disassembling tool.

16. The occlusal splint arrangement according to claim 1, in which the centering pin on the left side is provided with a first symbol and the centering pin on the right side is provided with a second symbol, the one of the splints being translucent at least in an area of each centering pin.

17. The occlusal splint arrangement according to claim 1, in which the exchangeable positioner of the left side and a centering pin corresponding to the exchangeable positioner on the left side are each provided with a first symbol and the exchangeable positioner of the right side and a centering pin corresponding to the exchangeable positioner on the right side are each provided with a second symbol.

18. The occlusal splint arrangement according to claim 1, in which associated pairs of exchangeable positioners for the left side and for the right side that have matching positions with respect to their centering recesses are provided with matching symbols, and that exchangeable positioners for the left side and right side with different positions with respect to their centring recesses are provided with different symbols.

19. The occlusal splint arrangement according to claim 14, in which a color of an outwards-facing side of a left attached positioner is different from a color of an outwards-facing side of a right attached positioner.

20. The occlusal splint arrangement according to claim 1, in which a outwards-facing side of the exchangeable positioner of the left side and an outwards-facing side of the exchangeable positioner of the right side are given different colors that match colors of a corresponding attached positioner of the left side and a corresponding attached positioner of the right side, respectively.

21. The occlusal splint arrangement according to claim 1, in which matching pairs of exchangeable positioners for the left side and for the right side are given matching colors on inwards-facing sides of the matching pairs of exchangeable positioners, and non-matching exchangeable positioners for the left side and the right side are given different colors on inwards-facing sides of the non-matching exchangeable positioners.

* * * * *

UNITED STATES PATENT AND TRADEMARK OFFICE
CERTIFICATE OF CORRECTION

PATENT NO. : 10,660,783 B2
APPLICATION NO. : 15/129134
DATED : May 26, 2020
INVENTOR(S) : Konrad Hofmann

Page 1 of 1

It is certified that error appears in the above-identified patent and that said Letters Patent is hereby corrected as shown below:

In the Claims

Column 18, Claim 20, Line 29, "which a outward-facing" should be -- which an outward-facing --.

Signed and Sealed this
Seventh Day of July, 2020

Andrei Iancu
*Director of the United States Patent and Trademark Office*